(12) United States Patent
Fukushi et al.

(10) Patent No.: US 11,207,003 B2
(45) Date of Patent: Dec. 28, 2021

(54) WALKING STATE DETERMINATION DEVICE, WALKING STATE DETERMINATION SYSTEM, WALKING STATE DETERMINATION METHOD, AND STORAGE MEDIUM

(71) Applicant: NEC Corporation, Tokyo (JP)

(72) Inventors: Kenichiro Fukushi, Tokyo (JP); Hisashi Ishida, Tokyo (JP); Takeo Nozaki, Tokyo (JP)

(73) Assignee: NEC CORPORATION, Tokyo (JP)

( * ) Notice: Subject to any disclaimer, the term of this patent is extended or adjusted under 35 U.S.C. 154(b) by 315 days.

(21) Appl. No.: 16/313,226

(22) PCT Filed: Jun. 29, 2017

(86) PCT No.: PCT/JP2017/023890
§ 371 (c)(1),
(2) Date: Dec. 26, 2018

(87) PCT Pub. No.: WO2018/003910
PCT Pub. Date: Jan. 4, 2018

(65) Prior Publication Data
US 2019/0150796 A1    May 23, 2019

(30) Foreign Application Priority Data
Jul. 1, 2016  (JP) .............................. JP2016-131187

(51) Int. Cl.
*A61B 5/11* (2006.01)
*A61B 5/103* (2006.01)
(Continued)

(52) U.S. Cl.
CPC .......... *A61B 5/1123* (2013.01); *A61B 5/1036* (2013.01); *A61B 5/11* (2013.01); *A61B 5/112* (2013.01); *A61B 5/1126* (2013.01); *A61B 5/4023* (2013.01); *A61B 5/6887* (2013.01); *A61B 5/1071* (2013.01); *A61B 2562/0219* (2013.01); *A61B 2562/0247* (2013.01); *A61B 2562/0261* (2013.01)

(58) Field of Classification Search
None
See application file for complete search history.

(56) References Cited

U.S. PATENT DOCUMENTS 5,511,571 A  *  4/1996  Adrezin .................... A61H 3/00
                                              135/66
6,011,481 A  *  1/2000  Luther ...................... A61H 3/02
                                              135/66
(Continued)

*Primary Examiner* — Sean P Dougherty
*Assistant Examiner* — Benjamin S Melhus
(74) *Attorney, Agent, or Firm* — Sughrue Mion, PLLC

(57) ABSTRACT

Provided is to determine a walking state when a target person uses a stick. A walking state determination device according to an embodiment of the present invention includes: an acquisition unit that acquires feature information indicating a feature of a motion of a target person when using a stick, based on first measurement data acquired from a first sensor installed at the stick and second measurement data acquired from a second sensor installed at the target person; and a determination unit that determines a walking state of the target person, based on the acquired feature information.

7 Claims, 11 Drawing Sheets

(51) Int. Cl.
*A61B 5/00* (2006.01)
*A61B 5/107* (2006.01)

(56) References Cited

U.S. PATENT DOCUMENTS

| | | | | |
|---|---|---|---|---|
| 8,007,450 | B2* | 8/2011 | Williams | A61B 5/1123 |
| | | | | 600/595 |
| 10,799,154 | B2* | 10/2020 | Sarkar | A45B 9/00 |
| 2007/0233403 | A1* | 10/2007 | Alwan | A61H 3/04 |
| | | | | 702/33 |
| 2009/0260426 | A1* | 10/2009 | Lieberman | A61B 5/1116 |
| | | | | 73/65.01 |
| 2011/0061697 | A1* | 3/2011 | Behrenbruch | G16H 20/30 |
| | | | | 135/66 |
| 2011/0205081 | A1* | 8/2011 | Chen | H04Q 9/00 |
| | | | | 340/870.01 |
| 2013/0346021 | A1* | 12/2013 | Stevens | G16H 40/63 |
| | | | | 702/160 |
| 2014/0276242 | A1* | 9/2014 | Chen | A61B 5/1116 |
| | | | | 600/595 |
| 2015/0282766 | A1* | 10/2015 | Cole | A61B 5/1038 |
| | | | | 702/139 |
| 2015/0325004 | A1 | 11/2015 | Utsunomiya et al. | |
| 2016/0253890 | A1* | 9/2016 | Rabinowitz | G09B 19/24 |
| | | | | 340/539.13 |
| 2016/0262661 | A1* | 9/2016 | Sarkar | A45B 3/00 |
| 2017/0224573 | A1* | 8/2017 | Challa | A45B 3/00 |
| 2019/0142120 | A1* | 5/2019 | AlGhazi | A45B 9/04 |
| | | | | 135/66 |

* cited by examiner

Fig.7

| FEATURE QUANTITY INDEX | WALKING DIFFICULTY LEVEL |
|---|---|
| EQUAL TO OR LARGER THAN 0 AND LOWER THAN 0.2 | LOW |
| EQUAL TO OR LARGER THAN 0.2 AND LOWER THAN 0.7 | MEDIUM |
| EQUAL TO OR LARGER THAN 0.7 AND EQUAL TO OR LOWER THAN 1.0 | HIGH |

| PARTIAL REGRESSION COEFFICIENTS | $\alpha_1$ | 0.54 |
| --- | --- | --- |
| | $\alpha_2$ | 0.36 |
| | ⋮ | ⋮ |
| | $\alpha_n$ | 0.51 |
| | $\beta$ | 0.77 |

| FEATURE QUANTITY INDEX | WALKING DIFFICULTY LEVEL |
|---|---|
| LOWER THAN −15 | LOW |
| EQUAL TO OR LARGER THAN −15 AND LOWER THAN 15 | MEDIUM |
| EQUAL TO OR LARGER THAN 15 | HIGH |

WALKING STATE DETERMINATION DEVICE, WALKING STATE DETERMINATION SYSTEM, WALKING STATE DETERMINATION METHOD, AND STORAGE MEDIUM

This application is a National Stage Entry of PCT/JP2017/023890 filed on Jun. 29, 2017, which claims priority from Japanese Patent Application 2016-131187 filed on Jul. 1, 2016, the contents of all of which are incorporated herein by reference, in their entirety.

TECHNICAL FIELD

The present invention relates to a walking state determination device, a walking state determination system, a walking state determination method, and a storage medium, for determining a walking state of a target person.

BACKGROUND ART

In order to appropriately support a target person such as an elderly person and a patient who receives rehabilitation, it is necessary to appropriately determine a walking state of the target person. As a method for acquiring walking data of a target person, PTL 1 discloses a technique of calculating data of a load acting on a subject, based on floor reaction force acquired by a force plate. Further, PTL 2 discloses a technique of analyzing a position of a landing point of a foot of a target person, based on image information of the target person.

CITATION LIST

Patent Literature

[PTL 1] Japanese Unexamined Patent Application Publication No. 2011-220908
[PTL 2] Japanese Unexamined Patent Application Publication No. 2015-042241

SUMMARY OF INVENTION

Technical Problem

Since such target persons often use sticks, it is necessary to appropriately determine a walking state when a target person uses a stick. The technique disclosed in PTL 1 merely acquires reaction force acting on a foot of a subject by acquiring all the floor reaction force and reaction force acting on a stick, and cannot determine a walking state when a stick is used, by only the reaction force. Further, the technique disclosed in PTL 2 merely analyzes a stick-landing position as a foot-landing position. For this reason, as a result, the walking state is merely determined based on the landing position of the foot, and a walking state when a target person uses a stick is not appropriately determined.

An object of the present invention is to solve the above-described problem, and to provide a walking state determination device and the like that can determine a walking state when a target person uses a stick.

Solution to Problem

An aspect of a walking state determination device of the present invention includes:

an acquisition unit that acquires feature information indicating a feature of a motion of a target person when using a stick, based on first measurement data acquired from a first sensor installed at the stick and second measurement data acquired from a second sensor installed at the target person; and a determination unit that determines a walking state of the target person, based on the acquired feature information.

An aspect of a walking state determination system of the present invention includes:

a first sensor installed at a stick;
a second sensor installed at a target person;
an acquisition unit that acquires feature information indicating a feature of a motion of a target person when using the stick, based on first measurement data acquired from the first sensor and second measurement data acquired from the second sensor; and a determination unit that determines a walking state of the target person, based on the acquired feature information.

An aspect of a walking state determination method of the present invention includes:

acquiring feature information indicating a feature of a motion of a target person when using a stick, based on first measurement data acquired from a first sensor installed at the stick and second measurement data acquired from a second sensor installed at the target person; and determining a walking state of the target person, based on the acquired feature information.

An aspect of a program of the present invention is that the program causes a computer to execute:

processing of acquiring feature information indicating a feature of a motion of a target person when using a stick, based on first measurement data acquired from a first sensor installed at the stick and second measurement data acquired from a second sensor installed at the target person; and processing of determining a walking state of the target person, based on the acquired feature information.

The program can be stored in a storage medium.

Advantageous Effects of Invention

According to the present invention, a walking state when a target person uses a stick can be determined.

BRIEF DESCRIPTION OF DRAWINGS

FIG. 7 is a diagram illustrating one example of determination index information according to the first example embodiment of the present invention.

EXAMPLE EMBODIMENT

Figure 1:
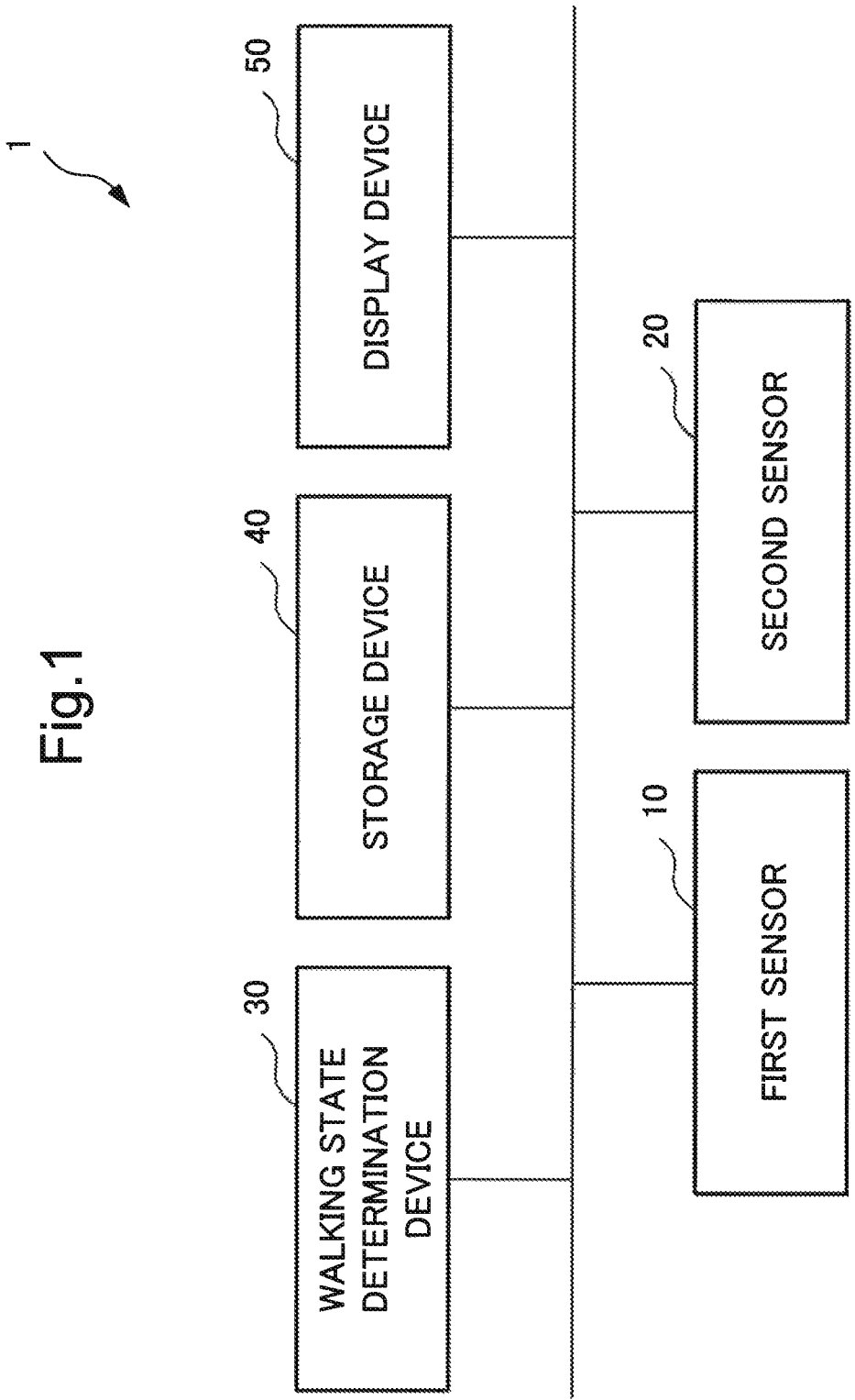
FIG. 1 is a diagram illustrating an operation form of the walking state determination system according to a first example embodiment of the present invention.

Hereinafter, an example embodiment of the present invention is described with reference to the drawings, but the present invention is not limited to the present example embodiment. Note that in the drawings described below, the same reference symbols are attached to the elements having the same functions, and the repetitive description thereof is sometimes omitted.

In the present example embodiment, the description is made by citing a walking state determination system (information processing system) as an example. The walking state determination system generates a feature quantity by using measurement data acquired from sensors installed at a target person and at a stick used by the target person. The walking state determination system determines a walking state of the target person by using the generated feature quantity.

FIG. 1 is a diagram illustrating an example of an operation form of walking state determination system 1 according to the first example embodiment of the present invention. As illustrated in FIG. 1, walking state determination system 1 according to the present example embodiment is configured. The configuration is made in such a way that first sensor 10, second sensor 20, walking state determination device 30, storage device 40, and display device 50 are connected to each other via a network such as the Internet and a local area network (LAN).

First sensor 10 (stick state measurement device) is a measurement device installed at an arbitrary position of a stick and detecting first measurement data that indicate a state of the stick. The first measurement data are movement characteristics such as a position, a height, a movement speed, acceleration, and an angle with respect to a vertical axis, of the stick, for example. The first measurement data are also a load acting on the stick, a state of contact with the ground, and a strength to hold a handle, for example. First sensor 10 is an inertial measurement unit (IMU), a smartphone, or a load sensor, for example. The IMU includes an accelerometer and an angular velocity meter. For example, first sensor 10 in the case of being an IMU detects, as the first measurement data, acceleration and an angular velocity of the stick at a predetermined time interval (period). Note that first sensor 10 in the case of being an IMU may detect, as the first measurement data, the maximum acceleration and the maximum angular velocity of the stick.

Hereinafter, the description is made by citing, as an example, the case where first sensor 10 according to the present example embodiment is a load sensor (pressure sensor). For example, first sensor 10 is installed at a stick tip (a tip portion, of the stick, on the side close to a ground contact surface). For example, first sensor 10 transmits the detected first measurement data to walking state determination device 30 via the network.

Note that first sensor 10 may be a pressure gauge such as a strain-gauge-type pressure gauge or an electrostatic-capacitance-type pressure gauge. For example, first sensor 10 in the case of being a pressure gauge has a measurement range including the maximum load in the axial direction. Further, first sensor 10 detects the first measurement data at a predetermined time interval (period). For example, first sensor 10 detects the first measurement data at an interval of five milliseconds.

Further, for example, first sensor 10 in the case of measuring an inclination of the stick axis with respect to the vertical axis is installed at an arbitrary position on the stick axis. This is because positional change in the stick axial direction does not affect the inclination.

Further, first sensor 10 may measure a plurality of pieces of the first measurement data. For example, first sensor 10 is installed at each of sticks used by a plurality of target persons, and the plurality of first sensors 10 detect the respective first measurement data. Thereby, relative evaluation can be performed on the subjects (target persons) in a groups formed of a plurality of the target persons. Concretely, since a user recognizes that a degree of walking difficulty of the target person is "the second out of the ten persons" for example, the user can easily understand a determined result of a walking state when the target person uses the stick. Further, for example, first sensor 10 is installed at each of a plurality of stick tips of a stick, such as a multi-point stick, that branches into a plurality of the stick tips, and the plurality of first sensors 10 measures the respective first measurement data. Thereby, a load acting on the stick can be recognized in more detail, and thus, accuracy of feature quantity generation can be improved.

Second sensor 20 (walking state measurement device) is a measurement device installed at an arbitrary position of the target person and detecting second measurement data that indicate a state of the target person. The second measurement data are a walking speed, a stride length, a step width, a joint angle, a toe height, a trunk-swing magnitude, a sole pressure, and a gravity center position of the target person, for example. Second sensor 20 is an IMU, a smartphone, or a load sensor, for example. For example, second sensor 20 in the case of being an IMU detects, as the second measurement data, acceleration and an angular velocity of a troubled foot of the target person at a predetermined time interval (period). Note that second sensor 20 in the case of being an IMU may detect, as the second measurement data, the maximum acceleration and the maximum angular velocity of a troubled foot of the target person.

Hereinafter, the description is made by citing, as an example, the case where second sensor 20 according to the present example embodiment is a load sensor (a pressure sensor such as a shoe-form load measurement device). Second sensor 20 is installed at a distal end portion (sole) of the troubled foot of the target person, for example. Second sensor 20 transmits, for example, the detected second measurement data to walking state determination device 30 via the network. Note that second sensor 20 according to the present example embodiment is installed at the troubled foot, but there is no limitation to this.

Note that second sensor 20 may be a pressure gauge such as a strain-gauge-type pressure gauge or an electrostatic-capacitance-type pressure gauge. For example, second sensor 20 in the case of being a pressure gauge has a measurement range including the maximum foot sole pressure (maximum load) in the axial direction. Further, second sensor 20 detects the second measurement data at a predetermined time interval (period). For example, second sensor 20 detects the second measurement data at an interval of five milliseconds.

Further, second sensor 20 in the case of measuring a toe height of the target person is installed at a toe portion of the target person, for example. In addition, for example, second sensor 20 in the case of measuring an inclination of the thigh with respect to the vertical axis is installed at an arbitrary position on the thigh. This is because the positional change of the thigh in the longitudinal direction does not affect the inclination.

Further, second sensor 20 may measure a plurality of pieces of the second measurement data. For example, the second sensors 20 are installed at respective distal end portions of troubled feet of a plurality of target persons, and detect the respective second measurement data. Thereby, relative evaluation can be performed on the subjects (target persons) in a group formed of a plurality of the target persons. Concretely, since a user recognizes that a degree of walking difficulty of the target person is "the second out of the ten persons" for example, the user can easily understand a determined result of a walking state when the target person uses the stick. Further, for example, the second sensors 20 are installed at respective tip portions of both feet, and the plurality of second sensors 20 each detect the second measurement data. Thereby, a load on the target person can be recognized in more detail, and thus, accuracy of feature quantity generation can be improved.

Walking state determination device 30 is a configuration relating to the essence of the present invention, and is an information processing device such as a personal computer (PC). The information processing device acquires feature information indicating a feature of a target person when using a stick, based on the first measurement data and the second measurement data. The information processing device determines a walking state of the target person, based on the acquired feature information. Hereinafter, information output by walking state determination device 30 is referred to as "output information". Details of walking state determination device 30 are described below.

Storage device 40 is a storage medium that stores determination index information used by walking state determination device 30 when determining a walking state of a target person. Details of the determination index information stored in storage device 40 will be described later.

Display device 50 is an interface of a user who uses walking state determination system 1 according to the present example embodiment. Display device 50 is implemented by installing, in a PC including a general information processing function, a software program for implementing a graphical user interface (GUI) and the like. Note that display device 50 may be an information processing device such as a tablet terminal or a wearable terminal for performing displaying of output information output from walking state determination device 30, and the like. For example, display device 50 displays a determined result of a walking state of the target person acquired by walking state determination device 30. Note that display device 50 may display related information in addition to the above-described determined result. The related information is the first measurement data, the second measurement data, and the feature information, for example.

Figure 2:
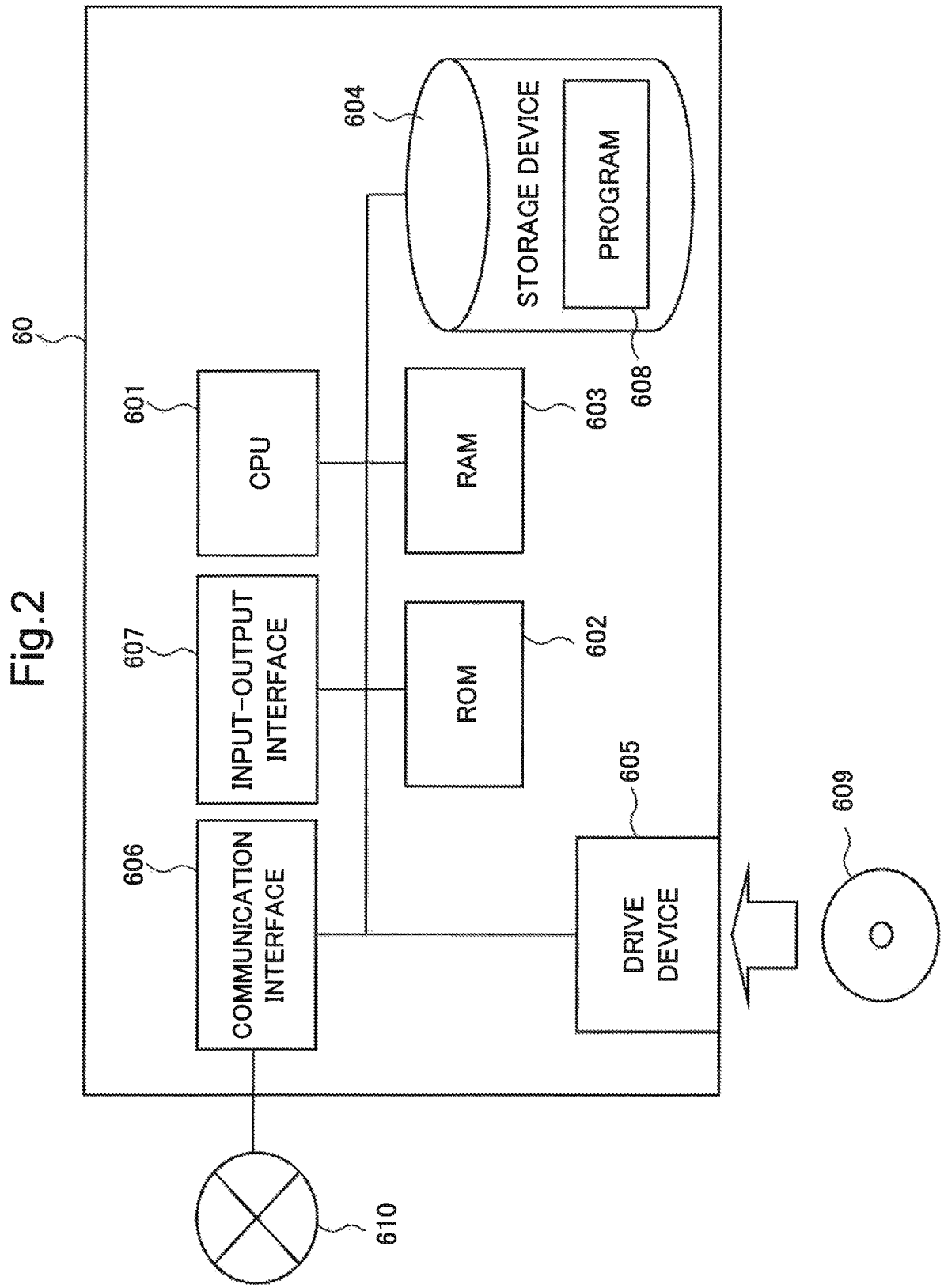
FIG. 2 is a block diagram illustrating a hardware configuration of a computer device that implements a walking state determination device and the like according to the present example embodiment.

Next, the description is made on hardware which constitutes each of the devices such as walking state determination device 30 and display device 50 included in walking state determination system 1 according to the present example embodiment. FIG. 2 is a block diagram illustrating a hardware configuration of computer device 60 that implements each of the devices such as walking state determination device 30 and display device 50 according to the present example embodiment.

As illustrated in FIG. 2, computer device 60 includes central processing unit (CPU) 601, read only memory (ROM) 602, random access memory (RAM) 603, storage device 604, drive device 605, communication interface 606, and input-output interface 607.

CPU 601 executes program 608 by using RAM 603. Program 608 may be stored in ROM 602. Further, program 608 may be recorded in a recording medium 609, and be read by drive device 605, or may be transmitted from an external device via network 610. Communication interface 606 exchanges data with an external device via network 610. Input-output interface 607 exchanges data with peripheral devices (such as a keyboard, a mouse, and a display device). Communication interface 606 and input-output interface 607 can function as a means for acquiring or outputting data. Data such as output information may be stored in storage device 604, or may be included in program 608.

Note that a processing method is also included in a category of each of the example embodiments. In the processing method, a program operating a configuration of the example embodiment in such a manner as to implement the functions of the following example embodiment is recorded in a recording medium. More specifically, a program for causing a computer to execute the processing illustrated in FIG. 5, FIG. 9, FIG. 10, or the like is recorded. And then, the program recorded in the recording medium is read out as codes, and is executed in a computer. In other words, the computer-readable recording medium is also included in the scope of each of the example embodiments. Further, the program itself as well as the recording medium in which the above-described program has been recorded are also included in each of the example embodiments.

Examples that can be used as the recording medium include a floppy (registered trademark) disk, a hard disk, an optical disk, a magneto-optical disk, a CD-ROM, a magnetic tape, a nonvolatile memory card, and a ROM. Further, a category of each of the example embodiments includes what executes the processing singly by the program recorded in the recording medium. Without limitation to this, a category of each of the example embodiments further includes what operates on an OS and performs the processing in cooperation with functions of other software and an expansion board.

First Example Embodiment

Figure 3:
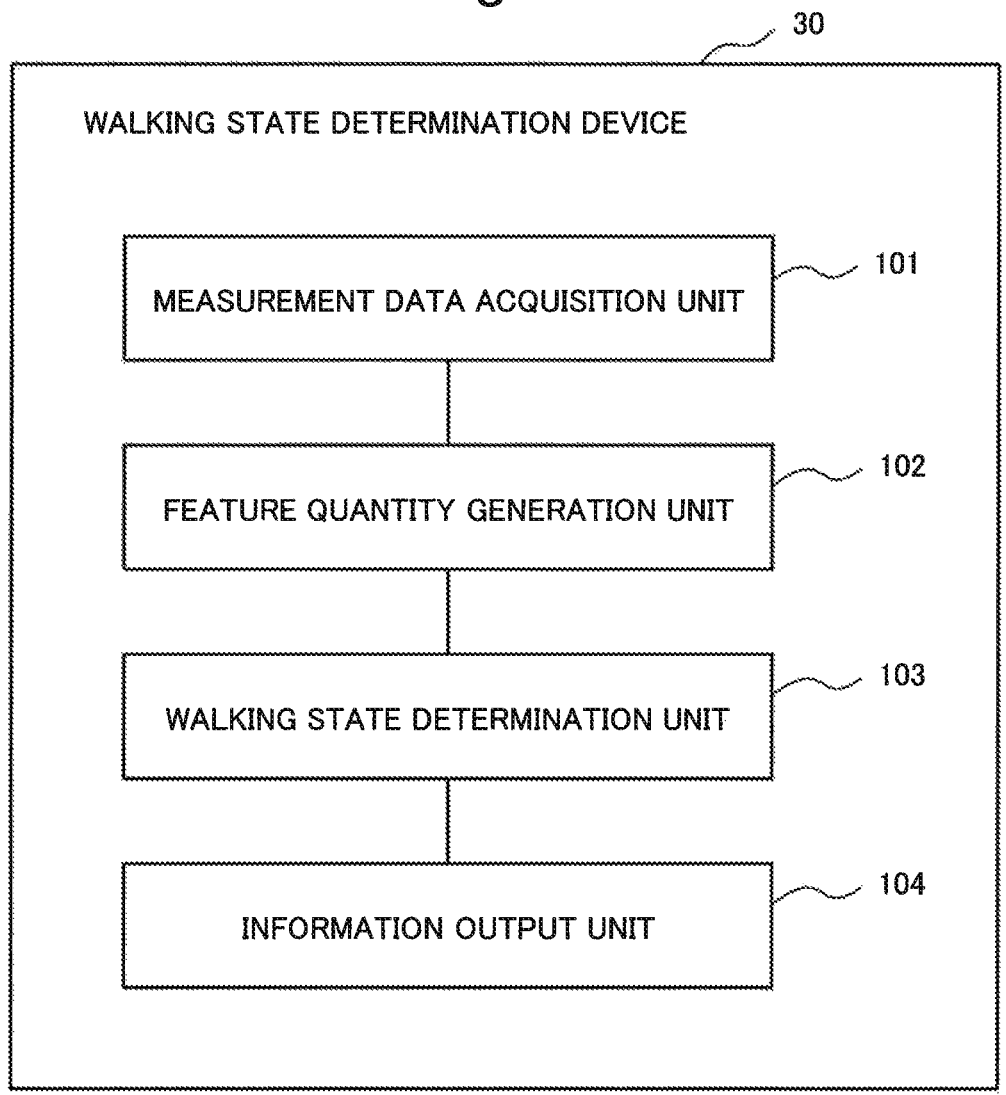
FIG. 3 is a block diagram illustrating a functional configuration of the walking state determination device according to the first example embodiment of the present invention.

Next, the description is made on a function of walking state determination device 30 according to the present example embodiment. FIG. 3 is a block diagram illustrating a functional configuration of walking state determination device 30 according to a first example embodiment of the present invention. The blocks illustrated in FIG. 3 may be mounted in a single device, or may be mounted separately in a plurality of devices. Data are transmitted and received between the blocks via an arbitrary means such as a data bus, a network, and a portable storage medium.

As illustrated in FIG. 3, walking state determination device 30 according to the present example embodiment includes measurement data acquisition unit 101 and feature quantity generation unit 102. The walking state determination device 30 also includes walking state determination unit 103 and information output unit 104.

Figure 4:
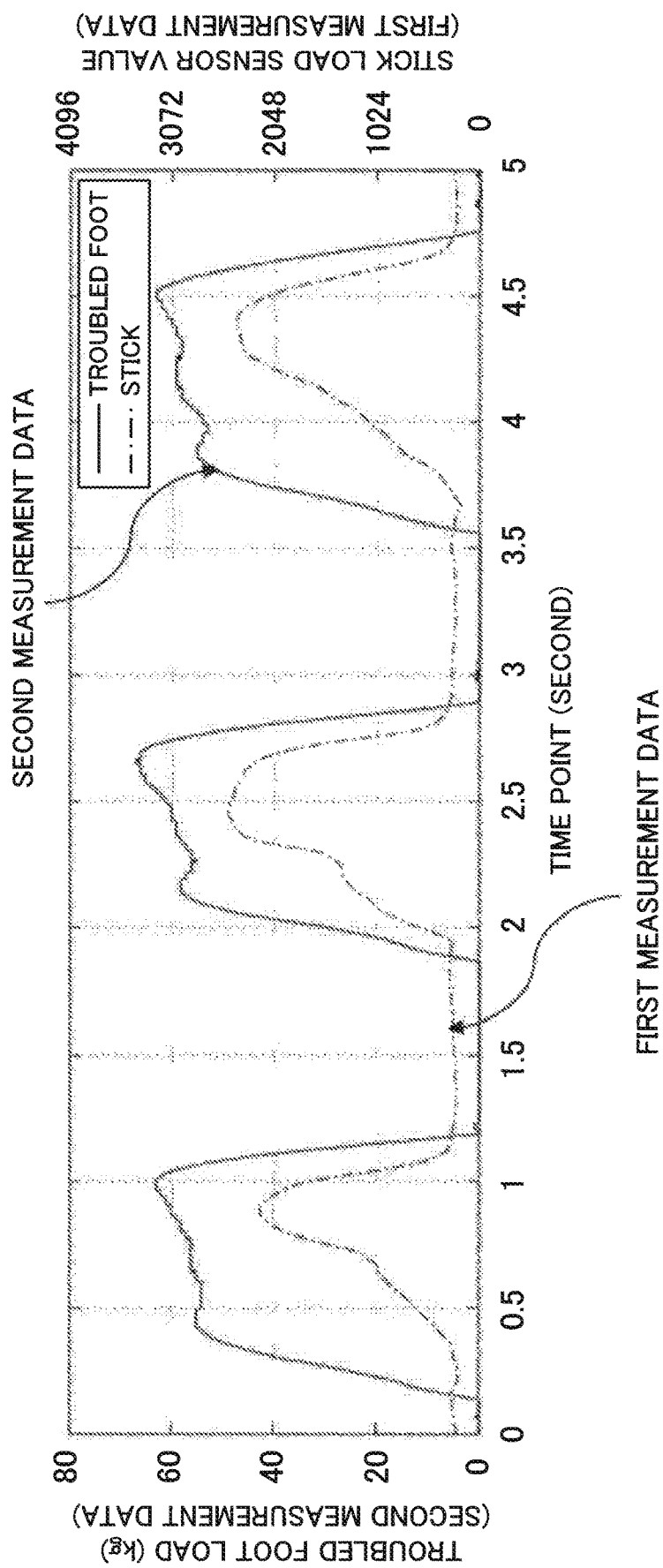
FIG. 4 is a diagram illustrating one example of a graph that indicates first measurement data and second measurement data acquired by a measurement data acquisition unit according to the first example embodiment of the present invention.

Measurement data acquisition unit 101 acquires the first measurement data and the second measurement data detected by first sensor 10 and second sensor 20. FIG. 4 is a diagram illustrating one example of a graph illustrating the first measurement data and the second measurement data acquired by measurement data acquisition unit 101 according to the first example embodiment of the present invention. In the graph illustrated in FIG. 4, the first measurement data are indicated by the one-dotted chain line, and the second measurement data are indicated by the solid line. Further, the horizontal axis of the graph illustrated in FIG. 4 represents a time point (second). The vertical axis on the right side of the graph represents a stick-load-sensor value related to the first measurement data, and the vertical axis on the left side of the graph represents a troubled foot load (kg) related to the second measurement data. A stick-load-sensor value is a load acting on a stick, and a troubled foot load is a load acting on a troubled foot of a target person. Note that as illustrated in FIG. 4, a stick-load-sensor value according to the present example embodiment is digital data in a range of 0 to 4095, for example.

Feature quantity generation unit 102 generates a stick walking feature quantity (hereinafter, written also as "feature quantity"), based on the respective measurement data acquired by measurement data acquisition unit 101. The feature quantity is a feature of a target person when using a stick. The feature quantity is a stick walking style index, for example. The stick walking style index indicates a walking style of the target person when using the stick. For example, the walking style index is a value indicating whether the walking style is three-motion walking or two-motion walking. Specifically, for example, the stick walking style index takes a value between zero and one. As a value of the stick walking style index is closer to one, a possibility of being the three-motion walking is higher, and as a value of the stick walking style index is closer to zero, a possibility of being the two-motion walking is higher.

The three-motion walking is a walking style of first advancing a stick forward, and next carrying a troubled foot and a healthy foot in this order. The two-motion walking is a walking style of advancing a stick and a troubled foot forward at the same time, and next advancing a healthy foot forward. In the three-motion walking, as compared with the two-motion walking, there is a tendency that a stride length and a pace are lowered, resulting in that a walking speed becomes slow, and thus, a walking difficulty degree is high. The walking difficulty degree is an index indicating a walking state of a target person. For example, the walking difficulty degree is a care necessity degree or a support necessity degree, a possibility of falling, and a self-walking degree (level) in walking out doors. Examples of the walking difficulty degree also include a Brunnstrom stage, a stroke impairment assessment set (SIAS), a pain scale, a fatigue degree, and a degree of compensatory movement.

Figure 5:
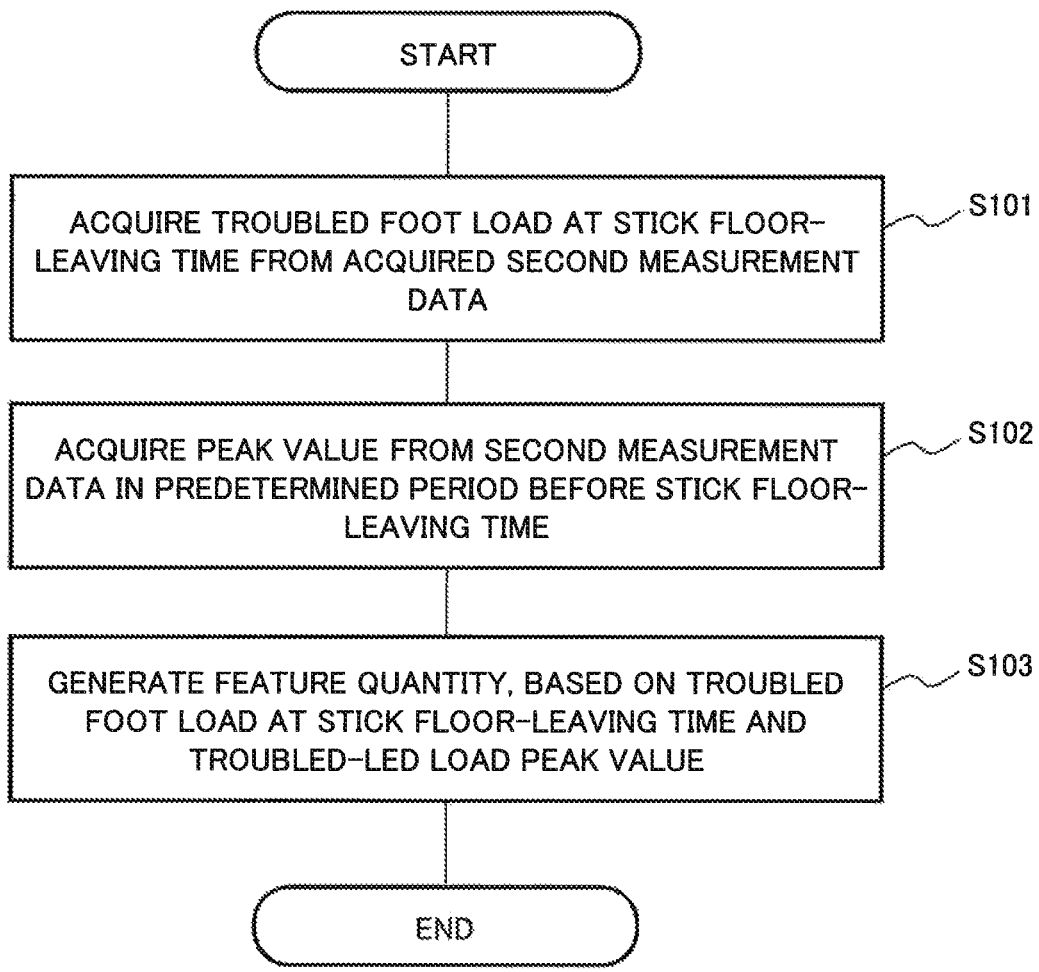
FIG. 5 is a flowchart illustrating an operation example of a feature quantity generation unit according to the first example embodiment of the present invention.
Figure 6:
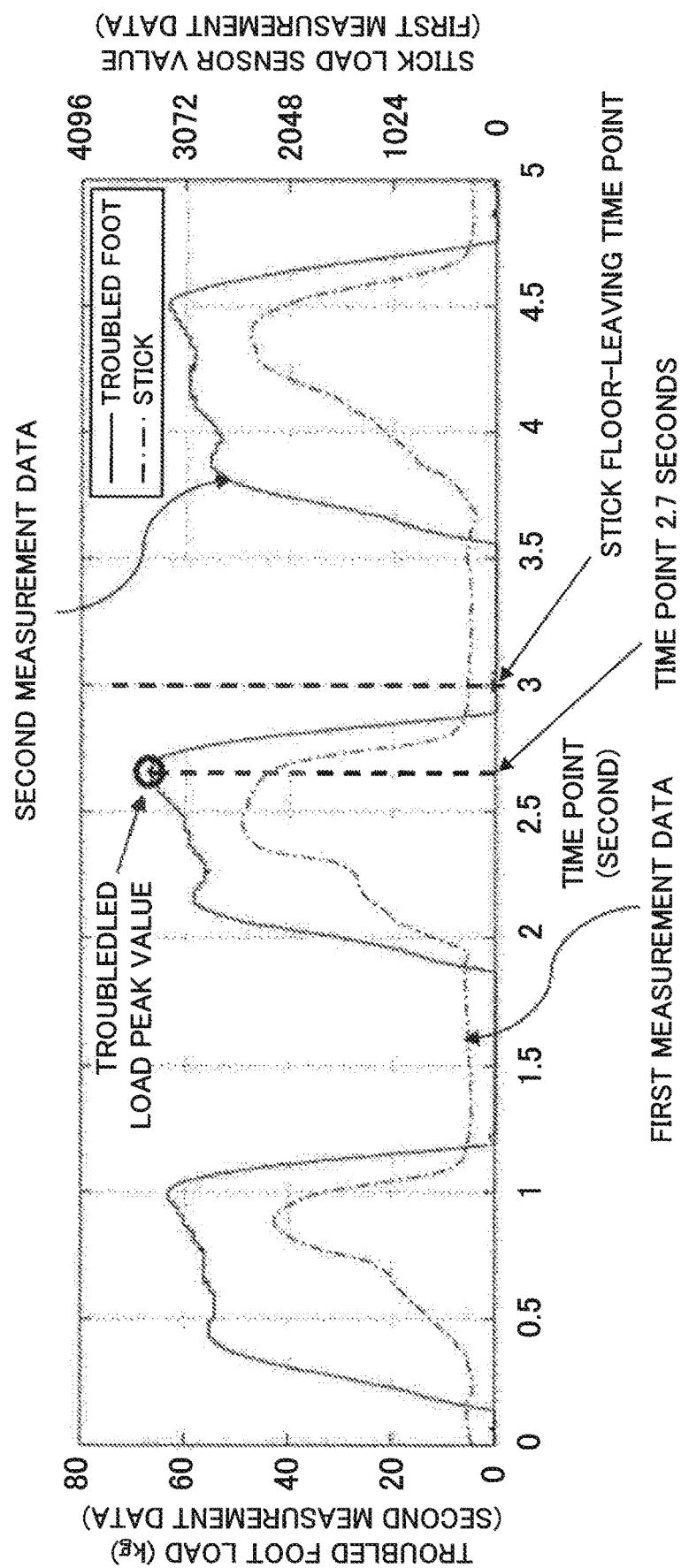
FIG. 6 is a diagram illustrating one example of a time point of a stick floor-leaving time and a peak value of a troubled foot load in a graph indicating first measurement data and second measurement data according to the first example embodiment of the present invention.

Hereinafter, the description is made on details of feature quantity generation processing by feature quantity generation unit 102. FIG. 5 is a flowchart illustrating an operation example of feature quantity generation unit 102 according to the first example embodiment of the present invention. From the second measurement data acquired by measurement data acquisition unit 101, feature quantity generation unit 102 acquires a troubled foot load at the stick floor-leaving time that is a timing when a stick leaves a floor (step S101). For example, the stick floor-leaving time is a timing when a value of the first measurement data becomes lower than a predetermined value (e.g., 285). FIG. 6 is a diagram illustrating one example of the time point at the stick floor-leaving time and a peak value of a troubled foot load in the graph. The graph indicates the first measurement data and the second measurement data according to the first example embodiment of the present invention. The graph illustrated in FIG. 6 indicates that the time point of 3.0 seconds when a stick load value becomes lower than 285 is the stick floor-leaving time, and a troubled foot load at the stick floor-leaving time is 1 kg.

Note that the stick floor-leaving time is described as the timing when a stick load value becomes lower than the predetermined value, but is not limited to this. For example, the stick floor-leaving time may be an arbitrary timing in a period during which a stick load value is lower than a predetermined value. The arbitrary timing is, for example, a central value or an average value of the period during which the first measurement data takes a value lower than the predetermined value.

Feature quantity generation unit 102 acquires a peak value of the second measurement data immediately before the stick floor-leaving time (step S102). For example, regarding the second measurement data illustrated in FIG. 6, feature quantity generation unit 102 acquires a troubled foot load (68 kg) at the time point of 2.7 seconds. This time point is a time point when the second measurement data takes a peak value (hereinafter, written also as "troubled-foot load peak value"). This time point is a time point is immediately before the time point (hereinafter, written also as "stick floor-leaving time point") of 3.0 seconds at the stick floor-leaving time.

Feature quantity generation unit 102 generates a feature quantity, based on the troubled foot load at the stick floor-leaving time and the troubled-foot load peak value acquired at S101 and S102 (step S103). For example, when generating a stick walking style index, feature quantity generation unit 102 uses the following equation.

Stick Walking Style Index=(Troubled foot Load at Stick Floor-Leaving Time)/(Troubled-foot Load Peak Value) (Equation 1)

For example, as illustrated in FIG. 6, the feature quantity when the troubled foot load at the stick floor-leaving time is 1 kg and the troubled-foot load peak value is 68 kg is 1/68, i.e., 0.015.

By such processing, feature quantity generation unit 102 calculates a feature quantity. In other words, feature quantity generation unit 102 that is an acquisition unit acquires feature information indicating a feature of a motion of a target person when using the stick. The acquisition is performed based on the first measurement data acquired from first sensor 10 installed at a stick and the second measurement data acquired from second sensor 20 installed at the target person.

Note that for example, the feature amount generation unit 102 acquires a stick walking style index. The acquisition is made by performing normalization in such a way that a difference between a time point of floor-landing of a stick and a time point of floor-landing of a troubled foot, a troubled foot load at the stick floor-landing time or at the troubled-foot floor-landing time, a stick load at the troubled-foot floor-landing time or at the troubled-foot floor-leaving time, or a combination thereof falls within a range from zero to one.

Walking state determination unit 103 determines a walking state of the target person, based on the feature quantity generated by feature quantity generation unit 102. Walking state determination unit 103 determines a walking state (walking difficulty degree (level)) of the target person. The determination is performed by using the feature quantity generated by feature quantity generation unit 102 and determination index information determined in advance. The determination index information determined in advance is information indicating correlation between a feature quantity and a walking difficulty degree, and is stored in storage device 40, for example. The determination index information is a table indicating association relation between a walking difficulty level and a stick walking feature quantity, for example.

FIG. 7 is a diagram illustrating one example of the determination index information according to the first example embodiment of the present invention. As illustrated in FIG. 7, the determination index information is a walking state determination table in which a feature quantity index indicating a predetermined range of a feature quantity is associated with a walking difficulty level. The walking state determination table represents that as a value of the feature quantity index (a stick walking style index in the present example embodiment) is larger (closer to one), the walking difficulty level becomes higher. The walking state determination table represents that as the value of the feature quantity index is smaller (closer to zero), the walking difficulty level becomes lower. As illustrated in FIG. 7, for example, the walking difficulty level when the feature quantity is 0.015 indicates "low". In other words, walking state determination unit 103 that is a determination unit determines a walking state of a target person, based on the acquired feature information.

Note that the determination index information is described above as the walking state determination table of the feature quantity index and the walking difficulty level, but is not limited to this. For example, the determination index information may be a walking state determination table in which a feature quantity index is associated with a self-walking level in walking out doors. The self-walking level in walking out doors represents a level being able to walk in outdoors by a target person. In other words, walking difficulty levels "low", "medium", and "high" in the present example embodiment are associated with the self-walking levels in walking out doors; that are "high", "medium", and "low", respectively.

Information output unit 104 outputs a result (a walking difficulty degree in the present example embodiment) determined by walking state determination unit 103, to display device 50. Note that information output unit 104 may output not only the determined result but also the walking state determination table associated with the generated feature quantity.

Figure 8:
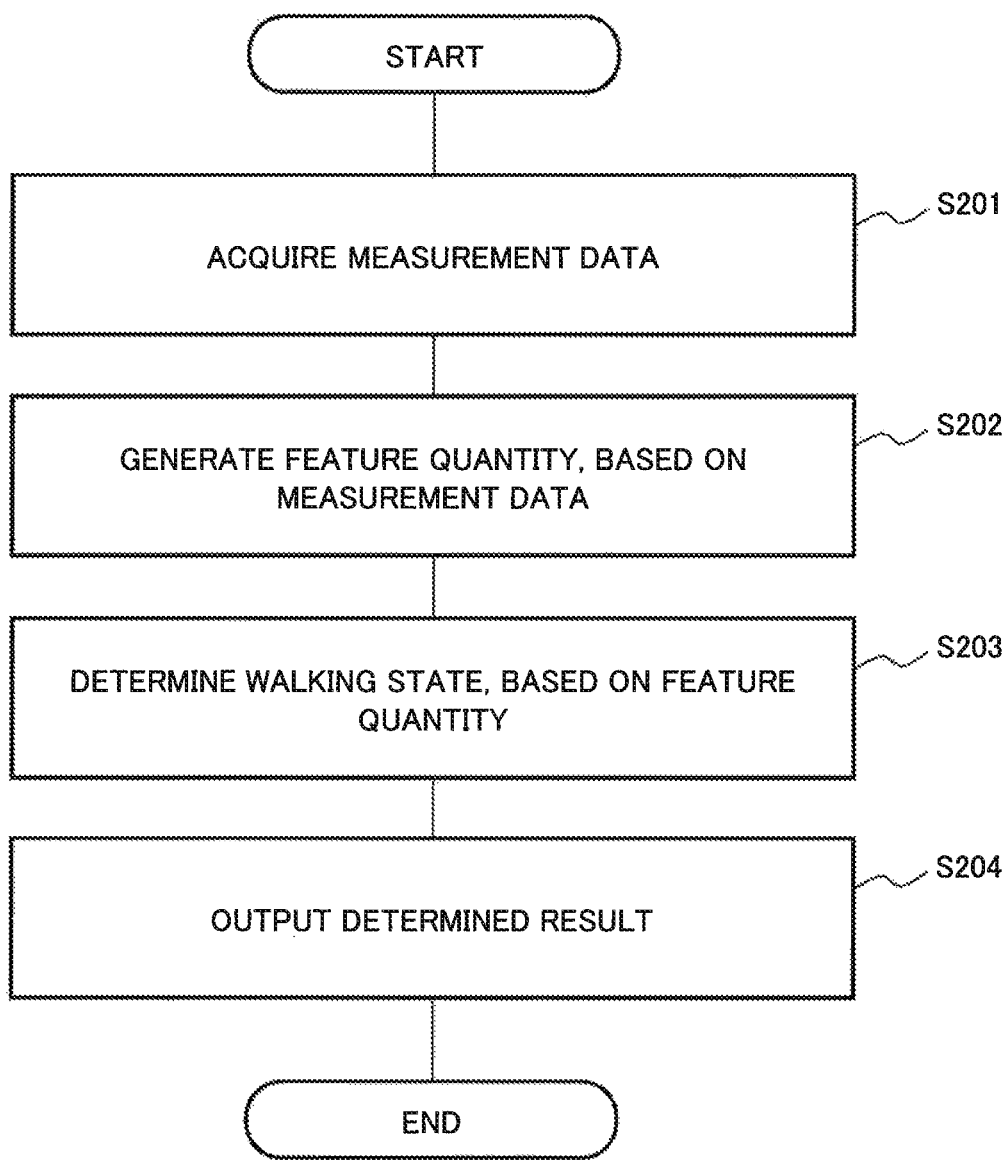
FIG. 8 is a flowchart illustrating an operation example of the walking state determination device according to the first example embodiment of the present invention.

Next, the description is made on an operation of walking state determination device 30 according to the present example embodiment. FIG. 8 is a flowchart illustrating an operation example of walking state determination device 30 according to the first example embodiment of the present invention.

Measurement data acquisition unit 101 acquires the first measurement data and the second measurement data acquired from first sensor 10 and second sensor 20 (step S201). Feature quantity generation unit 102 generates a feature quantity, based on the respective measurement data acquired by measurement data acquisition unit 101 (step S202). Walking state determination unit 103 determines a walking state, based on the feature quantity generated by feature quantity generation unit 102 (step S203). Information output unit 104 outputs the determined result (step S204).

As described above, walking state determination system 1 according to the present example embodiment acquires the first measurement data and the second measurement data acquired from first sensor 10 and second sensor 20. Then, walking state determination system 1 generates a feature quantity, based on the respective acquired measurement data, determines a walking state, based on the generated feature quantity, and outputs the determined result.

Thereby, a walking state of a target person is determined by using a feature quantity generated from the first measurement data and the second measurement data acquired from the sensor installed at a stick and the sensor installed at the target person. Thus, a walking state when the target person uses the stick can be determined.

Further, walking state determination system 1 according to the present example embodiment can quantify a walking difficulty degree in stick walking. Thus, walking state determination system 1 can support determination of time of discharge from a hospital, certification of care necessity (support necessity), and the like that is made by the user.

Furthermore, first sensor 10 and second sensor 20 are built-in sensors that can be installed at a stick and a target person. Thus, walking state determination system 1 according to the present example embodiment can determine a walking state of the target person anywhere. In addition, walking state determination system 1 according to the present example embodiment outputs a determined result to display device 50 such as a tablet terminal, and display device 50 displays the determined result. Thus, a user can refer to the determined result at an arbitrary place.

Note that the above description in which walking state determination unit 103 according to the present example embodiment determines a walking state, based on a walking state determination table illustrated in FIG. 7 is made. However, there is no limitation to this. The determination index information is a regression model (such as linear regression, a k-nearest neighbor algorithm, a neural network, or support vector regression) and coefficients thereof, for example. Alternatively, the determination index information is a classification model of a classification model (such as Bayes classification, a k-nearest neighbor algorithm, a decision tree, a random forest, a neural network, or a support vector machine) and coefficients thereof, for example. For example, walking state determination unit 103 determines a walking state (walking difficulty level), based on the following calculation equation by using generated feature quantities and partial regression coefficients.

$$\text{Walking Difficulty Level} = \alpha_1 \times (\text{Feature Quantity 1}) + \alpha_2 \times (\text{Feature Quantity 2}) + \ldots + \alpha_n \times (\text{Feature Quantity } n) + \beta \quad \text{(Equation 2)}$$

Figures 9, 10:
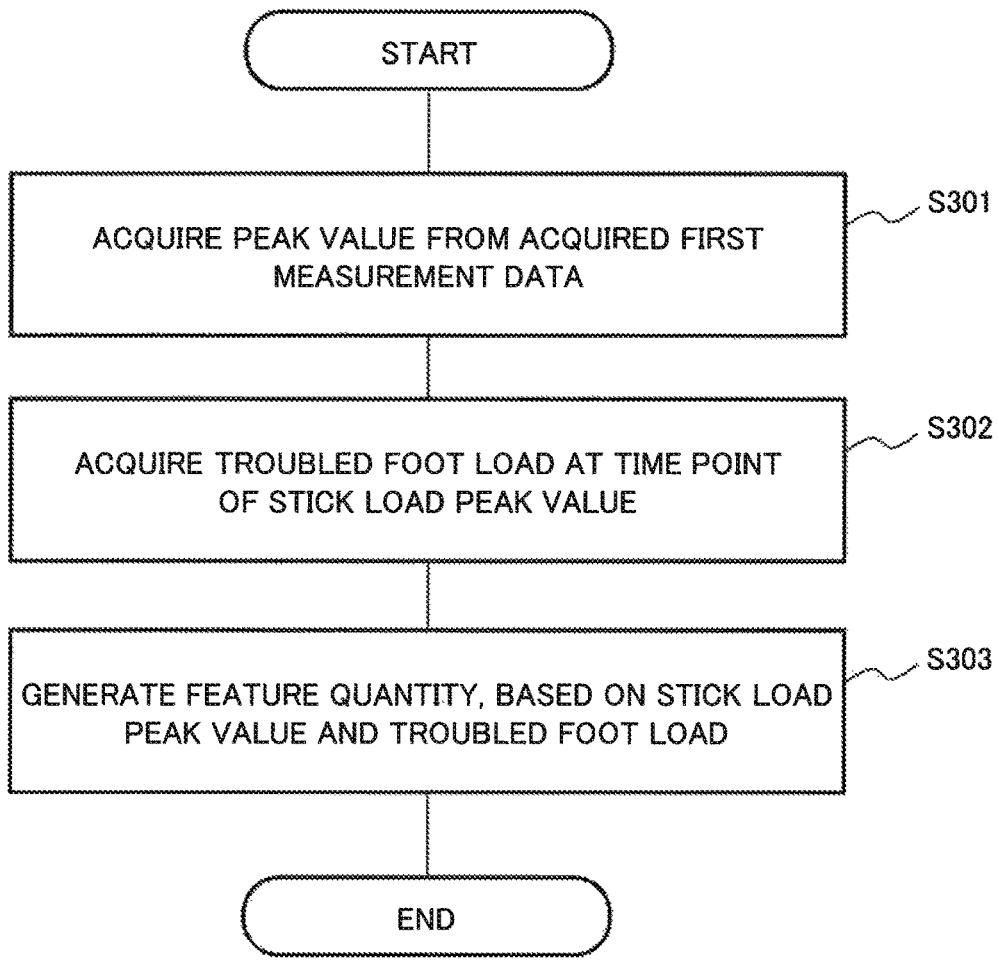
FIG. 9 is a diagram illustrating one example of partial regression coefficients according to the first example embodiment of the present invention.
FIG. 10 is a flowchart illustrating an operation example of a feature quantity generation unit according to a modified example of the first example embodiment of the present invention.

The above (Expression 2) is a regression equation in which feature quantities are set as explanatory variables, and a walking difficulty level is set as an objective variable. FIG. 9 is a diagram illustrating one example of partial regression coefficients according to the first example embodiment of the present invention. For example, walking state determination unit 103 calculates a walking difficulty level by using the regression equation expressed in the above (Equation 2) and the partial regression coefficients illustrated in FIG. 9. Thereby, walking state determination unit 103 determines a walking state.

Further, information output unit 104 according to the present example embodiment may output a result determined by walking state determination unit 103 and a feature quantity generated by feature quantity generation unit 102. Thereby, a user can not only recognize the determined result, but also recognize, from a feature quantity, whether or not a target person is in two-motion walking or in three-motion walking. The user can more accurately present a walking state when the target person uses a stick. Note that information output unit 104 may output not only a determined result but also a walking style associated with a feature quantity.

Further, for example, walking state determination system 1 according to the present example embodiment may output, to display device 50, a plurality of determined results for the same target person. Specifically, for example, information output unit 104 outputs not only a result determined by walking state determination unit 103, but also a plurality of past determined results for the same target person. Furthermore, for example, information output unit 104 may output, as an improvement degree, a difference between a plurality of past determined results for the same target person. Thereby, a change in a walking state and an improvement degree of a walking faculty in a fixed time period for the target person are quantified, and setting of rehabilitation menu associated with the walking state of the target person by a user can be supported. In addition, motivation of the target person can be improved.

Modified Example of First Example Embodiment

Next, the description is made on functions of a modified example of walking state determination system 1 according to the first example embodiment. Walking state determination system 1 according to the present modified example differs from walking state determination system 1 according to the first example embodiment in functions of walking state determination device 30 and storage device 40. Walking state determination device 30 according to the present modified example differs from walking state determination device 30 according to the first example embodiment in the functions of feature quantity generation unit 102 and walking state determination unit 103.

Feature quantity generation unit 102 in the present modified example generates a stick dependence degree that is a feature quantity, based on the first measurement data and the second measurement data. The stick dependence degree indicates a degree of dependence on a stick in walking when a target person uses the stick. Examples of the stick dependence degree include a ratio between a stick load and a troubled foot load in a troubled-foot standing term, joint angles of a troubled foot and a healthy foot, right and left balance at the time of walking, a combination thereof.

Figure 11:
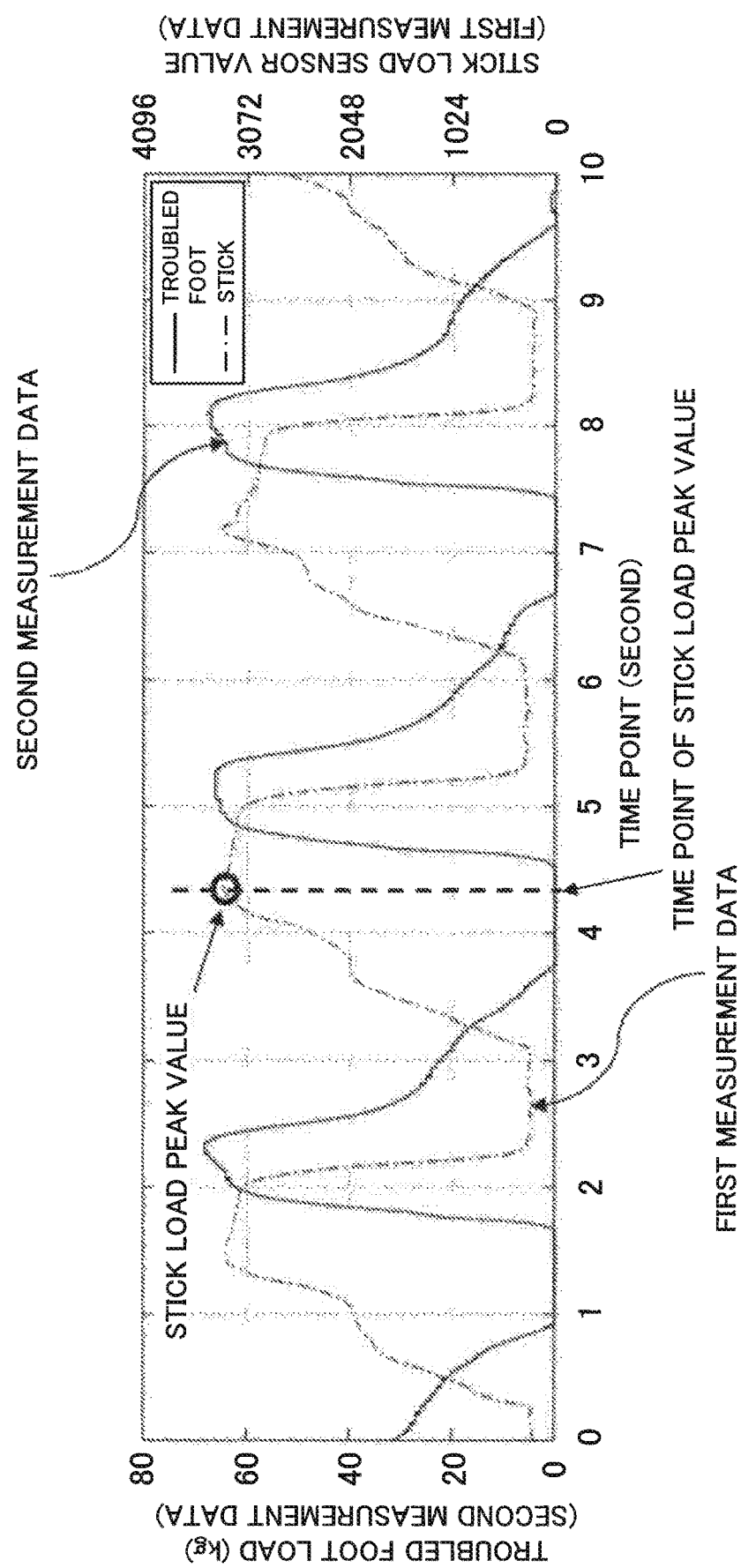
FIG. 11 is a diagram illustrating one example of a stick load peak value and a time point of the peak value in a graph that indicates first measurement data and second measurement data according to the modified example of the first example embodiment of the present invention.

Hereinafter, the detailed description is made on the feature quantity generation processing by feature quantity generation unit 102 in the present modified example. FIG. 10 is a flowchart illustrating an operation example of feature quantity generation unit 102 in the present modified example. Feature quantity generation unit 102 of the present modified example acquires a peak value (maximum stick-load-sensor value) from the first measurement data acquired by measurement data acquisition unit 101 (step S301). FIG. 11 is a diagram illustrating one example of a stick load peak value and a time point of the peak value in the graph. The graph indicates the first measurement data and the second measurement data according to the modified example of the first example embodiment of the present invention. The graph illustrated in FIG. 11 indicates that the time point of the peak value of the acquired first measurement data is 4.3 seconds, and indicates that the peak value is 3264.

Feature quantity generation unit 102 of the present modified example acquires a troubled foot load at a time point of a peak value of the first measurement data (step S302). As illustrated in FIG. 11, feature quantity generation unit 102 of the present modified example acquires a troubled foot load (0 kg) at 4.3 seconds, i.e., the time point of the stick load peak value.

Feature quantity generation unit 102 of the present modified example generates a feature quantity, based on the stick load peak value and the troubled foot load acquired at S101 and S102 (step S303). For example, when generating a stick dependence degree, feature quantity generation unit 102 of the present modified example uses the following equation. Here, $l_{stick}$ indicates the stick load peak value, and $l_{foot}$ indicates the troubled foot load at the time point of the stick load peak value.

$$\text{Stick Dependence Degree} = 0.011 \times l_{stick} - l_{foot} \quad \text{(Equation 3)}$$

As illustrated in the above (Equation 3), a stick dependence degree is acquired by subtracting a troubled foot load at a time point of a stick load peak value from a value of a product of a stick load peak value and 0.011. As illustrated in FIG. 11, when the stick load peak value is 3328, and the troubled foot load at the time point of the stick load peak value is 0 kg, the feature quantity is "0.011×3264−0", i.e., 35.9.

By such processing, feature quantity generation unit 102 calculates a stick dependence degree that is a feature quantity.

Figures 12, 13:
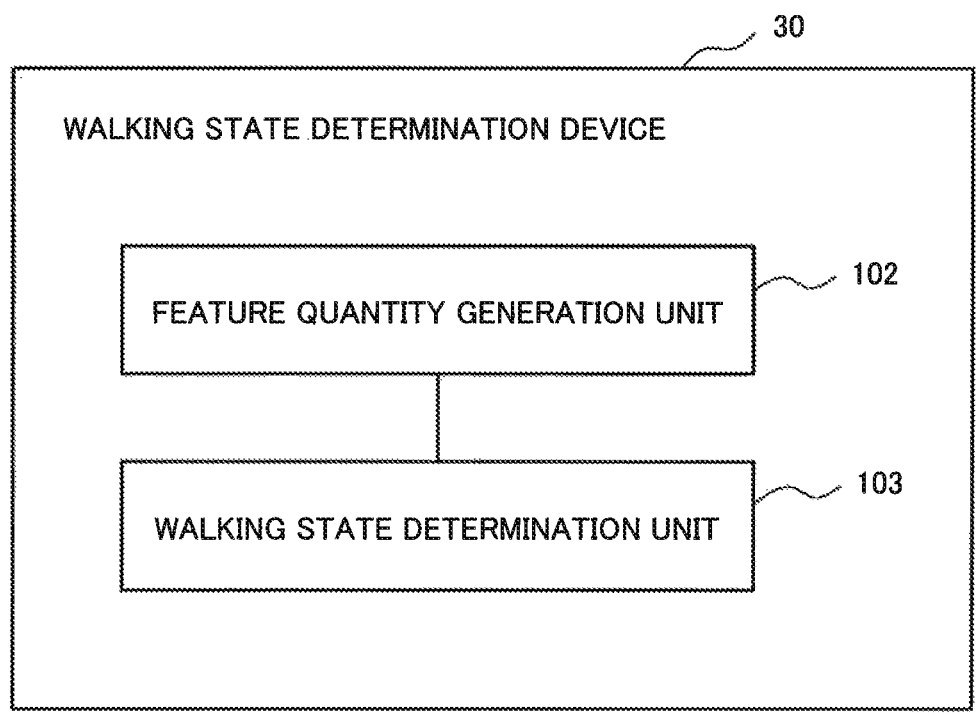
FIG. 12 is a diagram illustrating one example of determination index information according to the modified example of the first example embodiment of the present invention.
FIG. 13 is a block diagram of the walking state determination device according to each of the example embodiment of the present invention and the modified example.

Walking state determination unit 103 of the present modified example determines a walking state of a target person, based on a feature quantity generated by feature quantity generation unit 102 and the determination index information. FIG. 12 is a diagram illustrating one example of the determination index information according to the modified example of the first example embodiment of the present invention. As illustrated in FIG. 12, in a walking state determination table of the present modified example, a feature quantity index (a stick dependence degree in the present modified example) is associated with a walking difficulty level. The walking state determination table of the present modified example is the determination index information. The walking state determination table of the present modified example represents that as a value of the feature quantity index (the stick dependence degree in the present example embodiment) is larger (e.g., equal to or larger than 15), the walking difficulty level becomes higher. The walking state determination table represents that as a value of the feature quantity index is smaller (e.g., lower than −15), the walking difficulty level becomes lower. As illustrated in FIG. 12, for example, the walking difficulty level when the feature quantity is 35.9 indicates "high". The walking difficulty level that is "high" represents that a walking state of a target person is difficult.

Note that the determination index information is described above as a walking state determination table of a feature quantity index and a walking difficulty level, but there is no limitation to this. For example, the determination index information may be a walking state determination table in which a feature quantity index is associated with a self-walking level in walking out doors.

As described above, walking state determination system 1 according to the present modified example acquires the first measurement data and the second measurement data acquired from first sensor 10 and second sensor 20. Walking state determination system 1 generates a stick dependence degree that is a feature quantity, based on the respective acquired measurement data, determines a walking state, based on the generated stick dependence degree, and outputs the determined result.

Thereby, a walking state of a target person is determined by using a stick dependence degree. The stick dependence degree is generated from the first measured data and the second measurement data acquired from the sensor installed at a stick and the sensor installed at a target person. Thus, a walking state when the target person uses the stick can be determined.

Other Example Embodiments

FIG. 13 is a schematic configuration diagram of walking state determination device 30 according to each of the above-described example embodiment and modified example. FIG. 13 illustrates an example of a configuration in which walking state determination device 30 functions as a device. The device acquires feature information indicating a feature of a motion of a target person when using a stick, based on the first measurement data acquired from the sensor installed at the stick and the second measurement data acquired from the second sensor installed at the target person. The device determines a walking state of the target person, based on the feature information.

Walking state determination device 30 includes feature quantity generation unit 102 and walking state determination unit 103. Feature quantity generation unit 102 is an acquisition unit that acquires feature information indicating a motion of a target person when using a stick. The acquisition is performed based on the first measurement data acquired from the sensor installed at the stick and the second measurement data acquired from the second sensor installed at the target person. Walking state determination unit 103 determines a walking state of the target person, based on the acquired feature information.

The present invention is described above with reference to the respective example embodiments, but the present invention is not limited to the above-described example embodiments. Various modifications that can be understood by those skilled in the art can be made on a configuration and details of the present invention, within the scope of the present invention.

This application claims priority based on Japanese Patent Application No. 2016-131187 filed on Jul. 1, 2016, the disclosure of which is incorporated herein in its entirety.

REFERENCE SIGNS LIST

1 Walking state determination system
10 First sensor
20 Second sensor
30 Walking state determination device
40 Storage device
50 Display device
60 Computer device
101 Measurement data acquisition unit
102 Feature quantity generation unit
103 Walking state determination unit
104 Information output unit
601 CPU
602 ROM
603 RAM
604 Storage device
605 Drive device
606 Communication interface
607 Input-output interface
608 Program
609 Recording medium
610 Network

What is claimed is:

1. A walking state determination device comprising:
a memory and one or more processors executing a program loaded on the memory, wherein the one or more processors are configured to:
acquire first measurement data from a first sensor, which measures a stick load, installed at a stick and second measurement data from a second sensor, which measures a troubled foot load, installed at a target person who uses the stick;
calculate a difference, as a stick dependence degree, between a value of a peak value multiplied by a predetermined value and a troubled foot load acquired from the second measurement data at a time point of the peak value, wherein
the peak value is acquired from the first measurement data,
the stick dependence degree is a feature information indicating a feature of a motion of the target person when using the stick,
the stick dependence degree indicates a degree of dependence on the stick in walking when the target person uses the stick, and
the stick dependence degree increases when a value of the peak value multiplied by predetermined value is larger than the troubled foot load at the time point; and
determine a walking state of the target person, based on the stick dependence degree.

2. The walking state determination device according to claim 1, wherein the one or more processors are configured to
further determine that walking of the target person is more difficult as the stick dependence degree is higher.

3. The walking state determination device according to claim 2, the one or more processors are further configured to output a determined result.

4. The walking state determination device according to claim 1, the one or more processors are further configured to output a determined result.

5. The walking state determination device according to claim 4, wherein the one or more processors are configured to further output
a plurality of past determined results of the target person.

6. A walking state determination method comprising:
acquiring first measurement data from a first sensor, which measures a stick load, installed at a stick and second measurement data from a second sensor, which measures a troubled foot load, installed at a target person who uses the stick;
calculate a difference, as a stick dependence degree, between a value of a peak value multiplied by a predetermined value and a troubled foot load acquired from the second measurement data at a time point of the peak value, wherein the peak value is acquired from the first measurement data, the stick dependence degree is a feature information indicating a feature of a motion of the target person when using the stick, the stick dependence degree indicates a degree of dependence on the stick in walking when the target person uses the stick, and the stick dependence degree increases when a value of the peak value multiplied by predetermined value is larger than the troubled foot load at the time point; and determining a walking state of the target person, based on the stick dependence degree.

7. A walking state determination method comprising:

acquiring first measurement data from a first sensor, which measures a stick load, installed at a stick and second measurement data from a second sensor, which measures a troubled foot load, installed at a target person who uses the stick;

calculate a difference, as a stick dependence degree, between a value of a peak value multiplied by a predetermined value and a troubled foot load acquired from the second measurement data at a time point of the peak value, wherein the peak value is acquired from the first measurement data, the stick dependence degree is a feature information indicating a feature of a motion of the target person when using the stick, the stick dependence degree indicates a degree of dependence on the stick in walking when the target person uses the stick, and the stick dependence degree increases when a value of the peak value multiplied by predetermined value is larger than the troubled foot load at the time point; and determining a walking state of the target person, based on the stick dependence degree.

* * * * *